(12) United States Patent
Nishigishi

(10) Patent No.: US 10,617,541 B2
(45) Date of Patent: Apr. 14, 2020

(54) STENT

(71) Applicant: PENTAS Inc., Tokyo (JP)

(72) Inventor: Makoto Nishigishi, Tokyo (JP)

(73) Assignee: PENTAS Inc., Tokyo (JP)

( * ) Notice: Subject to any disclaimer, the term of this patent is extended or adjusted under 35 U.S.C. 154(b) by 92 days.

(21) Appl. No.: 16/075,463

(22) PCT Filed: Feb. 22, 2017

(86) PCT No.: PCT/JP2017/006519
§ 371 (c)(1),
(2) Date: Aug. 3, 2018

(87) PCT Pub. No.: WO2017/146081
PCT Pub. Date: Aug. 31, 2017

(65) Prior Publication Data
US 2019/0046340 A1    Feb. 14, 2019

(30) Foreign Application Priority Data

Feb. 25, 2016 (JP) .................... 2016-033784

(51) Int. Cl.
*A61F 2/88*    (2006.01)
*A61F 2/90*    (2013.01)
*A61L 31/02*    (2006.01)

(52) U.S. Cl.
CPC ............. *A61F 2/88* (2013.01); *A61F 2/90* (2013.01); *A61L 31/022* (2013.01); *A61F 2250/0018* (2013.01); *A61F 2250/0019* (2013.01); *A61F 2250/0029* (2013.01)

(58) Field of Classification Search
CPC ..................................... A61F 2/88; A61F 2/90
USPC ........................................ 623/1.15, 1.5–1.53
See application file for complete search history.

(56) References Cited

U.S. PATENT DOCUMENTS

2012/0265294 A1    10/2012    Nishigishi
2014/0288637 A1    9/2014    Clerc

FOREIGN PATENT DOCUMENTS

DE    102015107291 A1    9/2015
JP    2012223209 A    11/2012

OTHER PUBLICATIONS

International Search Report dated May 16, 2017 filed in PCT/JP2017/006519.

*Primary Examiner* — Suzette J Gherbi
(74) *Attorney, Agent, or Firm* — Rankin, Hill & Clark LLP

(57) ABSTRACT

A strand made of a platinum alloy material is prevented from protruding from both ends of a stent when some strands of the stent are disposed using the strand made of the platinum alloy material. In a stent (10) which is formed by helicoidally braiding a plurality of strands, some strands among the plurality of strands are disposed using a strand made of a platinum alloy material, and a length of the strand made of the platinum alloy material is made shorter than lengths of other strands by a length of the strand made of the platinum alloy material which is estimated to protrude from the stent.

5 Claims, 3 Drawing Sheets (A)

(B)

STENT

TECHNICAL FIELD

The present invention relates to a stent.

BACKGROUND ART

There is known a stent for medical purpose as follows. The stent is formed by helicoidally braiding a plurality of strands (see Patent Literature 1).

CITATION LIST

Patent Literature

Patent Literature 1: JP 2012-223209 A

SUMMARY OF INVENTION

Technical Problem

In recent years, a stent formed by helicoidally braiding, a plurality of strands is used for the purpose of medical treatment of an aneurysm. As a strand of the stent, metal strands such as a stainless steel, a Co—Cr alloy (cobalt-chromium alloy), a Ni—Ti alloy (nickel-titanium alloy) are generally used. These materials have a transmissive property with respect to an X ray. Therefore, the stent implanted in a blood vessel of a patient may be not captured at the time of an X-ray photography, and thus it is not possible to check the implantation position of the stent of the patient. Therefore, there is considered to dispose some strands made of a platinum alloy material which is the transmissive property with respect to the X ray among the plurality of strands. However, the strand made of the platinum alloy material has a probability by nature to protrude from both ends of the stent when the stent extends.

Solution to Problem

According to a first aspect of the invention, a stent is formed by helicoidally braiding a plurality of strands. Some strands among the plurality of strands are disposed using a strand made of a platinum alloy material. A length of the strand made of the platinum alloy material is made shorter than lengths of other strands by a length of the strand made of the platinum alloy material which is estimated to protrude from the stent.

According to a second aspect of the invention, the stent of the first aspect is configured such that some even-numbered strands among the plurality of strands are disposed using a strand made of the platinum alloy material.

According to a third aspect of the invention, the stent of the second aspect is configured such that two strands among the plurality of strands are disposed using a strand made of the platinum alloy material.

According to a fourth aspect of the invention, the stent of the first to third aspects is configured such that strands in the same winding direction among the plurality of strands are disposed using the strand made of the platinum alloy material.

According to a fifth aspect of the invention, the stent of the first to fourth aspects is configured such that the plurality of strands are strands made of a cobalt-chromium alloy material, and the strand made of the platinum alloy material is a strand made of a platinum-iridium alloy material.

Advantageous Effects of Invention

According to the invention, a length of the strand made of the platinum alloy material is made shorter than lengths of other strands by a length of the strand made of the platinum alloy material which is estimated to protrude from the stent. Therefore, it is possible to prevent the strand made of the platinum alloy material from protruding from both ends of the stent.

DESCRIPTION OF EMBODIMENTS

Figure 1:
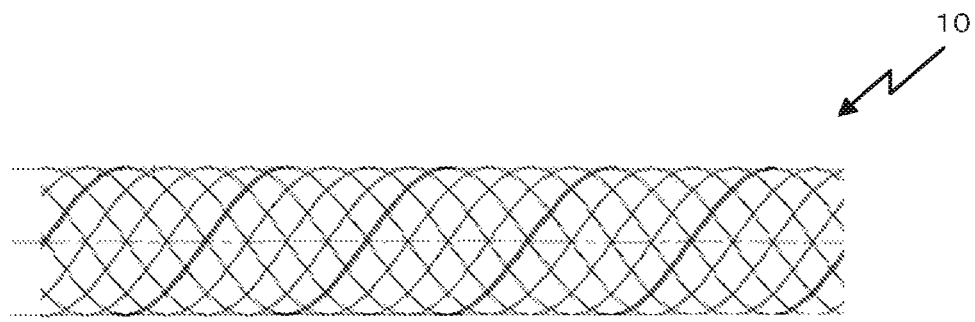
FIG. 1 is a diagram schematically illustrating a shape of a stent formed by helicoidally braiding a plurality of strands.

FIG. 1 is a diagram schematically illustrating a shape of a stent in the embodiment. In the embodiment, a stent 10 is assumed to be formed by helicoidally braiding a plurality of strands as illustrated in FIG. 1. In the strand, for example, a metal material such as a stainless steel, a Co—Cr alloy (cobalt-chromium alloy), and a Ni—Ti alloy (nickel-titanium alloy) is used.

The stent 10 is formed by helicoidally braiding a plurality of metal strands. The number of strands of the stent 10 has a plurality of types. For example, a 16-strand stent formed by braiding 16 strands, a 24-strand stent formed by braiding 24 strands, and a 32-strand stent formed by braiding 32 strands. Further, FIG. 1 illustrates the 16-strand stent.

In the stent 10 formed by helicoidally braiding the plurality of metal strands, the metal strand has a transmissive property with respect to an X ray. Therefore, at the time of an X-ray photography, the stent in a patient cannot be captured, and the implantation position of the stent of the patient cannot be checked. In the stent of the embodiment to solve such a problem, some strands among the plurality of strands of the stent are disposed using a strand made of a platinum alloy material having a non-transmissive property with respect to the X ray.

The embodiment will be described about a case where the strands (hereinafter, referred to as "Pt—Ir strand") made of a platinum-iridium alloy material are disposed such that a plurality of the strands (for example, 2 adjacent strands) are adjacent in the stent configured by strands (hereinafter, referred to as "Co—Cr strands") made of the cobalt-chromium alloy material.

Figure 2:
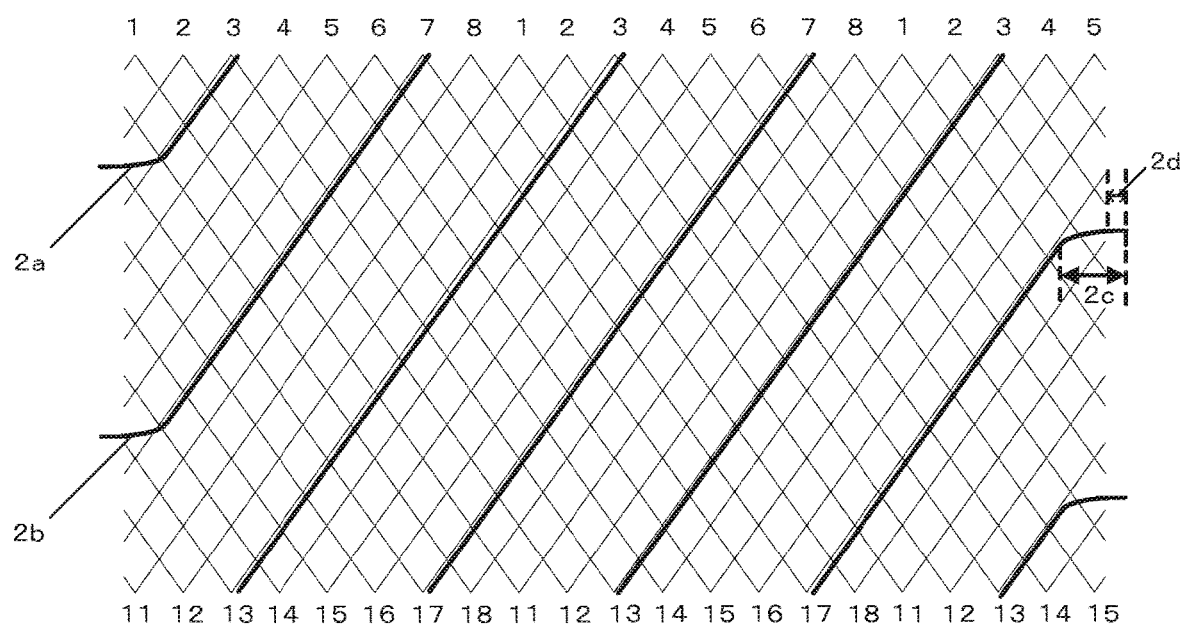
FIG. 2 is a diagram schematically illustrating an exemplary layout of a platinum alloy wire in a developed view of the stent.

FIG. 2 is a diagram schematically illustrating an exemplary layout of the Pt—Ir strands in a developed view of the 16-strand stent. In the example illustrated in FIG. 2, eight strands are braided in a first direction inclined on a right upper side and a second direction inclined on a left upper side. In FIG. 2, the numbers attached in the upper and lower portions of the developed view are only attached for the convenience' sake in order to help with understanding that the strands are continuously disposed, and there is no other meaning. The numbers attached on the upper portion of the developed view indicate that the strands are continuously disposed in the first direction inclining on the right upper side in FIG. 2. For example, the same number on the upper portion indicates one strand which is wound in the first direction. In addition, the number attached on the lower portion of the developed view indicates that the strands wound in the second direction inclined on the left upper side in FIG. 2 are continuously disposed. For example, the strands attached with the same number in the lower portion indicate one strand which is wound in the second direction.

In the embodiment, the even-numbered strands in the same winding direction among the Co—Cr strands of the stent are disposed using the Pt—Ir strands. In FIG. 2, a Pt—Ir strand 2a depicted with a thick line is disposed at a strand 3 wound in the first direction. A Pt—Ir strand 2b depicted with a thick line is disposed at a strand 7 wound in the first direction. In other words, in FIG. 2, two Pt—Ir strands 2a and 2b are disposed with respect to the Co—Cr strand 3 and the Co—Cr strand 7 wound in the first direction. In this way, it is preferable that two Pt—Ir strands be disposed in the stent as illustrated in FIG. 2 from the viewpoint of an even extending performance and an even extending force of the stent.

Herein, the description will be given about the reason why two Pt—Ir strands are disposed in the stent. Compared to the Co—Cr strand, the Pt—Ir strand is inferior in the extending performance. Therefore, the extending force of the stent can be secured as the number of the Pt—Ir strands disposed in the stent becomes small. In addition, when the number of the Pt—Ir strands disposed in the stent is set to an odd number, there is a concern that the stent does not extend evenly. Therefore, it can be said that an even number or two satisfying a condition as small as possible is optimal to the number of Pt—Ir strands.

Figure 3:
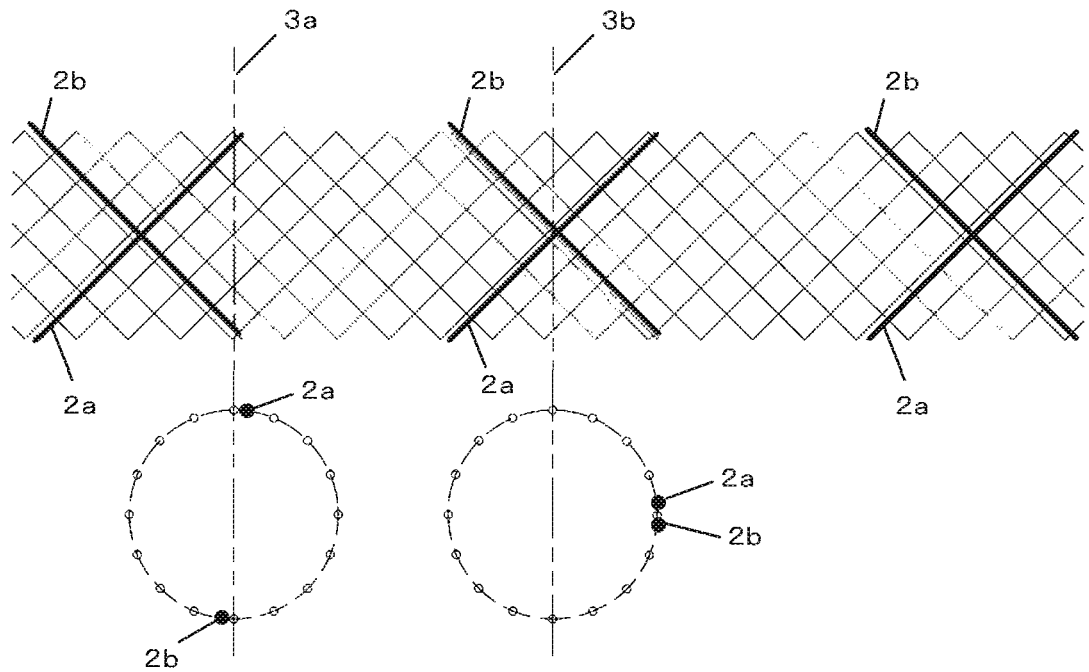
FIG. 3 is a diagram schematically illustrating an exemplary layout of the platinum alloy wire in a side view of the stent.
Figure 3:
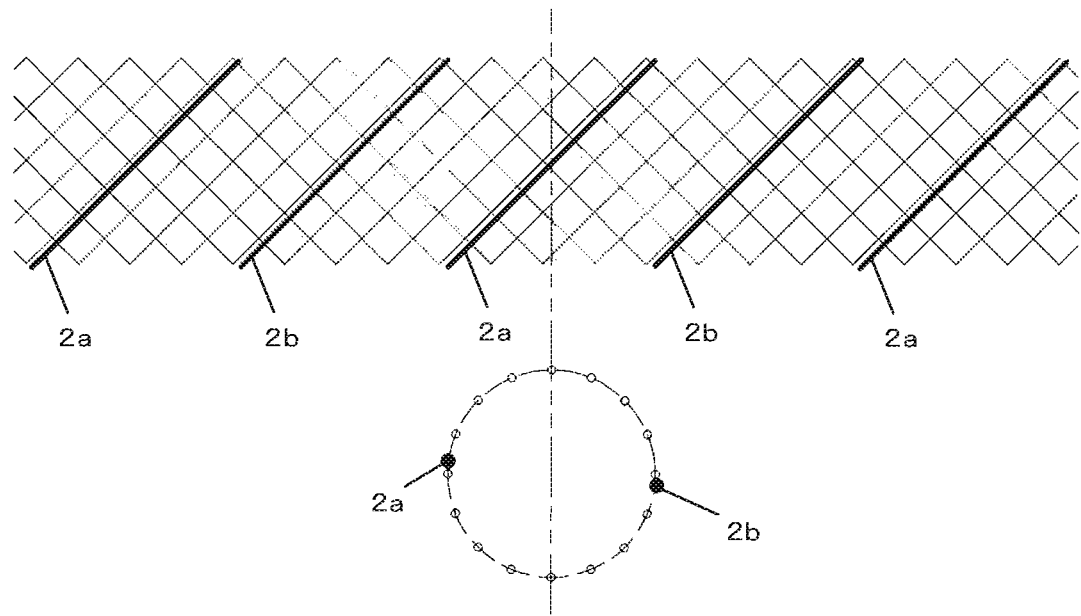

In addition, as illustrated in FIG. 2, the reason why two Pt—Ir strands are wound in the same direction is as follows. In a case where two Pt—Ir strands are disposed in different winding directions, an interval of two Pt—Ir strands is different depending on a portion of the stent as illustrated in FIG. 3(a). In other words, the interval between two Pt—Ir strands 2a and 2b is widened at a position 3a on the stent as illustrated in FIG. 3(a), but the interval between two Pt—Ir strands 2a and 2b becomes narrow at a position 3b. At a position where the interval between two Pt—Ir strands 2a and 2b becomes narrow as the position 3b, a portion between the Pt—Ir strands 2a and 2b is plastically deformed. Therefore, a cross-sectional shape of the stent at the position 3a and a cross-sectional shape of the stent at the position 3b are different. In this way, in a case where two Pt—Ir strands are disposed in different winding directions, the cross-sectional shape of the stent is changed depending on a position on the stent.

On the contrary, in a case where two Pt—Ir strands are disposed in the same winding direction at an equal interval, the interval between two Pt—Ir strands 2a and 2b is not changed regardless of a position as illustrated in FIG. 3(b). Therefore, the cross-sectional shape is not changed depending on a position on the stent. In the embodiment, Pt—Ir strands 2a and 2b are disposed in the same winding direction, so that it is prevented that the cross-sectional shape is changed depending on a position on the stent.

As the stent in the embodiment, there is a difference in nature between the Co—Cr strand and the Pt—Ir strand in the stent where the Pt—Ir strands are disposed. Therefore, in a case where the Co—Cr strand and the Pt—Ir strand are made to be the same length when the stent is manufactured, the Pt—Ir strand may protrude from the end of the stent when the stent extends. In other words, the Co—Cr strand and the Pt—Ir strand both have the spiral structure at the time when the stent is manufactured. However, once the stent is mounted in a delivery system, the shape is changed to be straight. Since the Co—Cr strand has an elastic deformation range even when being straight once, the Co—Cr strand is restored to the original spiral shape when the stent is taken out of a tube, and the stent extends.

On the other hand, the Pt—Ir strand keeps the straight shape even when the stent is taken out of the tube due to plastic deformation. In a single body, the Pt—Ir strand itself has no restoring force to return to the original spiral shape. However, the Pt—Ir strand is braided to form the stent together with the Co—Cr strand, and thus the Pt—Ir strand returns to the spiral shape by an elastic force of the Co—Cr strand. At this time, a braided portion of the Pt—Ir strand and the Co—Cr strand returns to the spiral shape due to the elastic force of the Co—Cr strand. However, free portions on both end sides are still kept in the straight shape and, as a result, the Pt—Ir strand protrudes from the ends of the Co—Cr strand.

In the embodiment, in order to prevent that the Pt—Ir strand protrudes from the both ends of the stent, a protruding length of the Pt—Ir strand is estimated in advance, and the Pt—Ir strand is made short by the estimated length. In the Pt—Ir strand, as illustrated in FIG. 2, a straight portion 2c is left on both ends, and a tip end 2d of the portion protrudes from the end of the stent. Therefore, in the embodiment, a cutting length is calculated to cut the length corresponding to the tip end 2d in the both ends of the Pt—Ir strand. Specifically, a shortening rate R of the Pt—Ir strand is calculated by the following Formula (1), and the cutting length of the Pt—Ir strand is obtained by the following Formula (2). Experimentally, it can be seen that the Pt—Ir strand protrudes by about 2 meshes of the stent. Therefore, in the following Formula (2), a value obtained by multiplying the shortening rate R to the length corresponding to 2 meshes of the stent is subtracted from the length corresponding to 2 meshes of the stent, so that the cutting length of the Pt—Ir strand is calculated. Further, in the following Formulas (1) and (2), "P" represents a pitch length of the stent, "I" represents a diameter of the stent, and "S" represents the number of strands of the stent.

[Mathematical Formula 1]

$$\frac{P}{\sqrt{P^2 + I^2}} = R \qquad (1)$$

[Mathematical Formula 2]

$$\frac{\sqrt{P^2 + I^2}}{2S} \times 2 - \frac{\sqrt{P^2 + I^2}}{2S} \times 2 \times R \qquad (2)$$

In the embodiment, the both ends of the Pt—Ir strand are cut to be short by the cutting length calculated by Formula (2) compared to the length of the Co—Cr strand. Therefore, it is possible to prevent that the Pt—Ir strand protrudes from the end of the stent when the stent extends.

According to the embodiment, the following operational effects can be obtained.

(1) In the stent formed by helicoidally braiding the plurality of strands, some strands of the plurality of strands are made of a platinum alloy material and are disposed. The length of the strand made of the platinum alloy material is shortened to be a length estimated for the strand made of the platinum alloy material to protrude from the stent. When the Co—Cr strand and the Pt—Ir strand are made to be the same length, the Pt-h strand may protrude from the end of the stent when the stent extends due to a different in nature between the Co—Cr strand and the Pt—Ir strand. However, with the configuration, it is possible to prevent that the Pt—Ir strand protrudes from the end of the stent.

(2) Some even-numbered strands among the plurality of strands are disposed using a Pt—Ir strand. With the configuration, it is possible to make the stent extend evenly when the stent extends.

(3) Two strands among the plurality of strands are disposed using a Pt—Ir strand. With this configuration, it is possible to dispose the Pt—Ir strands to make the stent extend evenly after an extending force of the stent is secured.

(4) Strands in the same winding direction among the plurality of strands are disposed using the Pt—Ir strand. With this configuration, it is possible to secure the same cross-sectional shape regardless of a position on the stent.

Modifications

Further, the stent of the embodiment may be modified as follows.

(1) In the above-described embodiment, the Pt—Ir strands made of a platinum-iridium alloy material are disposed as two strands made of a platinum alloy material disposed in the stent. However, the strand is not limited to the Pt—Ir strand as long as the material is suitable to dispose on the stent and an alloy containing platinum having a non-transmissive property with respect to the X ray is used.

(2) In the above-described embodiment, the description has been given about the example where the cutting length of the Pt-h strand is calculated by Formula (2). Formula (2) is an arithmetic expression to obtain the cutting length of the Pt—Ir strand by subtracting the length obtained by multiplying the shortening rate R to the length of the strands of 2 meshes from the length of the strands of 2 meshes on the basis of the experimental fact that the Pt—Ir strand protrudes from the stent by about 2 meshes. However, Formula (2) may be appropriately changed according to by how much length of meshes the Pt—Ir strand protrudes from the stent.

Further, the invention is not limited to any one of the configurations of the above-described embodiment as long as the characteristic functions of the invention are not degraded. In addition, the above-described embodiment and a plurality of modifications may be combined.

Priority is claimed on Japanese Patent Application No. 2016-33784 filed on Feb. 25, 2016, the content of which is incorporated herein by reference.

REFERENCE SIGNS LIST 10 stent
2a first platinum alloy wire
2b second platinum alloy wire

The invention claimed is:

1. A stent which is formed by helicoidally braiding a plurality of strands,
   wherein some strands among the plurality of strands are disposed using a strand made of a platinum alloy material, and
   wherein a length of the strand made of the platinum alloy material is made shorter than lengths of other strands by a length of the strand made of the platinum alloy material which is estimated to protrude from the stent.

2. The stent according to claim 1,
   wherein some even-numbered strands among the plurality of strands are disposed using the strand made of the platinum alloy material.

3. The stent according to claim 2,
   wherein two strands among the plurality of strands are disposed using the strand made of the platinum alloy material.

4. The stent according to claim 1,
   wherein strands to be wound in the same direction among the plurality of strands are disposed using the strand made of the platinum alloy material.

5. The stent according to claim 1,
   wherein the plurality of strands are strands made of cobalt-chromium alloy material, and
   wherein the strand made of the platinum alloy material is a strand made of a platinum-iridium alloy material.

* * * * *